United States Patent [19]

Norton et al.

[11] Patent Number: 5,163,966
[45] Date of Patent: Nov. 17, 1992

[54] BAR-HOLDING PROSTHETIC LIMB

[75] Inventors: William E. Norton; Thomas W. Vest; Jewell G. Belcher, Jr.; James R. Carden, all of Huntsville, Ala.

[73] Assignee: The United States of America as represented by the Administrator of the National Aeronautics and Space Administration, Washington, D.C.

[21] Appl. No.: 873,931
[22] Filed: Apr. 15, 1992
[51] Int. Cl.⁵ ............................................... A61F 2/54
[52] U.S. Cl. .......................................... 623/65; 623/57
[58] Field of Search ........................ 623/65, 57, 61, 62

[56] References Cited

U.S. PATENT DOCUMENTS

| 1,213,222 | 1/1917 | McKay | 623/65 X |
| 1,711,447 | 4/1929 | Colanduoni | 623/65 X |
| 2,427,974 | 9/1947 | Otterman | 623/62 |
| 2,561,523 | 7/1951 | Lux | 623/65 X |
| 3,735,426 | 5/1973 | Horvath | 623/65 |

Primary Examiner—Ronald Frinks
Attorney, Agent, or Firm—Robert L. Broad, Jr.; Guy M. Miller; John R. Manning

[57] ABSTRACT

A prosthetic limb (10) for a below-the-elbow amputee is constructed having a removable effector (16) removably mounted in a mount (18) having semicircular bands (20) set by "hand lapped" construction in sides of a body (12) near a closed end (22) thereof. The effector (16) is offset from the body (12) and is provided with supports (60, 62), each having a C-shaped slot (64, 66) for receiving a horizontally oriented bar, such as that on a chainsaw. A pair of semi-circular gripping members (68, 70) are pivotally mounted by pins (72, 74) near a closed end of the slots (64, 66) and are biased closed by a C-shaped leaf spring (90) disposed about an outer periphery of the members (68, 70).

14 Claims, 3 Drawing Sheets

BAR-HOLDING PROSTHETIC LIMB

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S. C. 2457).

FIELD OF THE INVENTION

This invention relates generally to prosthetic limbs for below-the-elbow amputees, and more particularly to such a limb adapted for lifting bars or tubular members such as the bar on a chainsaw.

BACKGROUND OF THE INVENTION

In the past, below-the-elbow amputees have had very few realistic choices available to them for assisting them in performing heavy duty tasks. Although so-called "bionic" prosthetics are available, drawbacks of these devices are numerous and include cost of the limb, which can easily run into the tens of thousands of dollars, cost of batteries, weight of the device, its durability, and the necessity to keep it internally clean and dry. As a result, these "bionic" devices have not been widely accepted by amputees, and prosthetic devices which utilize body motions to perform selected tasks are generally preferred. However, the pulleys, traction devices, and complexities of these type devices also have limitations with respect to cost, comfort, and durability. As a result, prosthetics tailored to a specific purpose appear to be best suited for an active amputee.

Of the prosthetic device of this last class, perhaps the closest to applicants' device is U.S. Pat. No. 1,711,447, issued on Apr. 30, 1929, to Colanduoni, which discloses a forearm prosthetic device having an axially inserted member with opposed leaf springs adapted to grip a ball mounted on a steering wheel of a vehicle or to a gear shifting rod. No provision is made in this prosthetic device to grip a tubular object. Another below-the-elbow device is disclosed in U.S. Pat. No. 1,213,222, issued on Jan. 23, 1917, to McKay, which discloses a prosthetic mount having an axial, splined mounting recess provided with a catch and a plurality of fittings, each with a specific purpose and each having a like, splined mount for mounting in the recess. One of the fittings disclosed in this patent (FIGS. 6 and 7) shows a spring-loaded clamp-like fitting disposed for holding a handle such as that found on a rake or shovel. However, the angle of the splined mount makes this fitting unsuitable for holding a chainsaw bar or other horizontal tubular member, Additionally, this fitting does not appear to possess the durability or structural rigidity necessary to perform heavy lifting.

In accordance with the foregoing, it is the object of this invention to provide a prosthetic device for a below-the-elbow amputee which is adapted to allow the amputee to easily work with horizontal tubular members such as the bar found on a chainsaw.

SUMMARY OF THE INVENTION

This invention is a prosthetic limb for a below-the-elbow amputee that will allow the amputee to lift or otherwise manipulate horizontal bars or tubes such as the bar on a chainsaw. The limb is constructed having a hollow body adapted to receive a stump of the forearm of the amputee and is provided with a mount having a receptacle offset from the body. An effector is mounted in the receptacle, the effector having a C-shaped slot facing forward of the body and constructed to support a load associated with the bar. A C-shaped gripping member for gripping the bar is pivotally disposed in the effector to partially close the slot and is provided with biasing means to bias the gripping member closed.

DETAILED DESCRIPTION OF THE DRAWINGS

Figure 1:
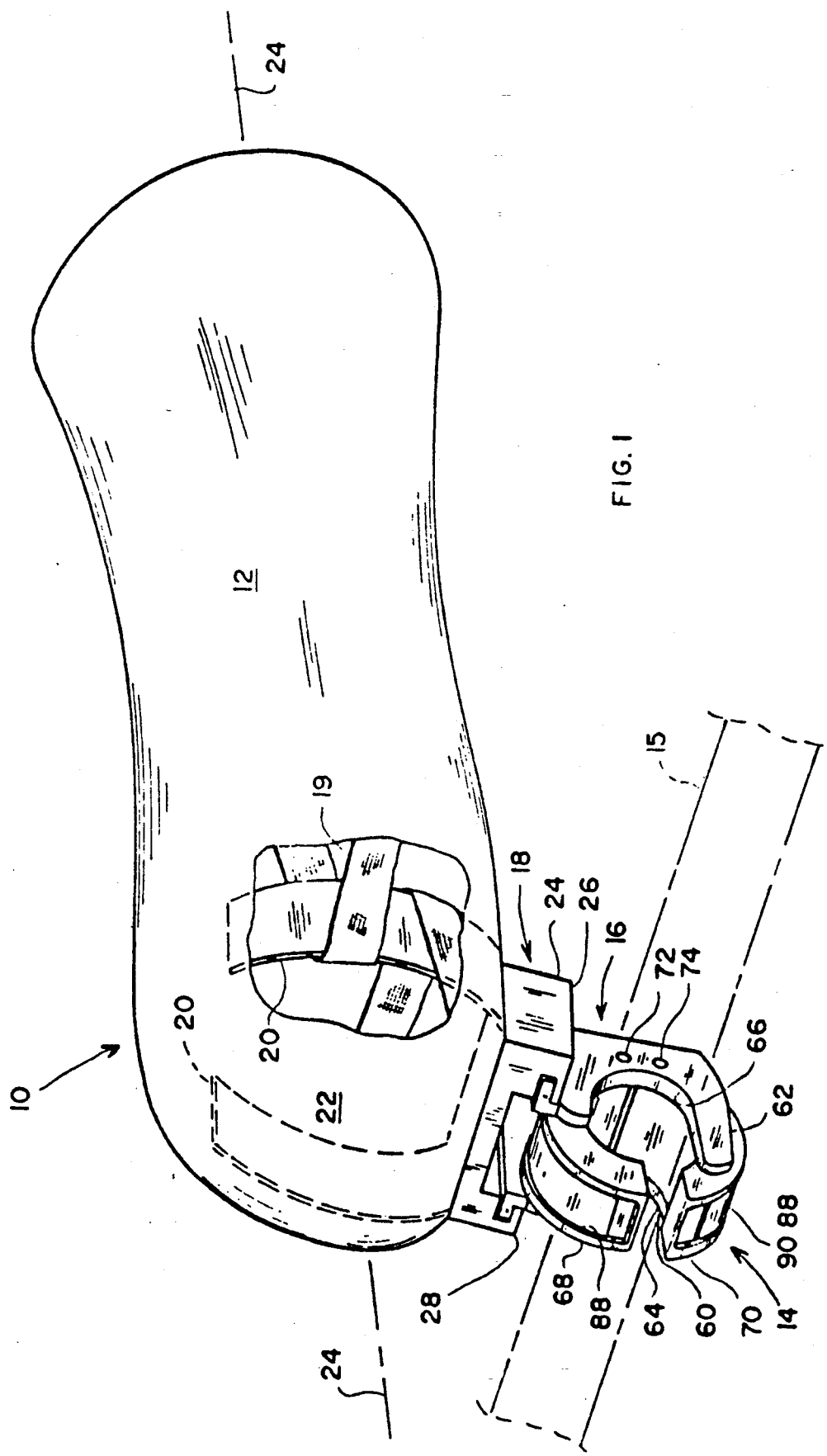
FIG. 1 is a perspective view partially out away of a prosthetic limb of the present invention.

Referring initially to FIG. 1, a prosthetic device 10 is shown for a below-the-elbow amputee, the device being adapted to allow the amputee to easily work with horizontal tubular objects such as the bar on a chainsaw, the handle of a push cart, dumb bells involved with weight lifting, etc., this bar being illustrated in FIG. 1 by dashed lines 15. In this device, a cast-like, hollow body 12 is constructed to fit over the stump of the wearer's forearm and is conventionally held in place with straps (not shown) particular to those found in the art. Body 12 is also constructed to allow lifting of heavy objects and yet be as lightweight as possible. One example of such construction is found in the manufacture of higher-quality recreational boat hulls wherein fiberglass netting impregnated with uncured, liquid resin mixed with hardener is placed on a core to form the hull. This "hand-lapped" construction in a prosthetic limb, yields a strong, durable, lightweight device with a fitting, or effector assembly 14, that will not become loose due to vibration or heavy use.

Figure 2:
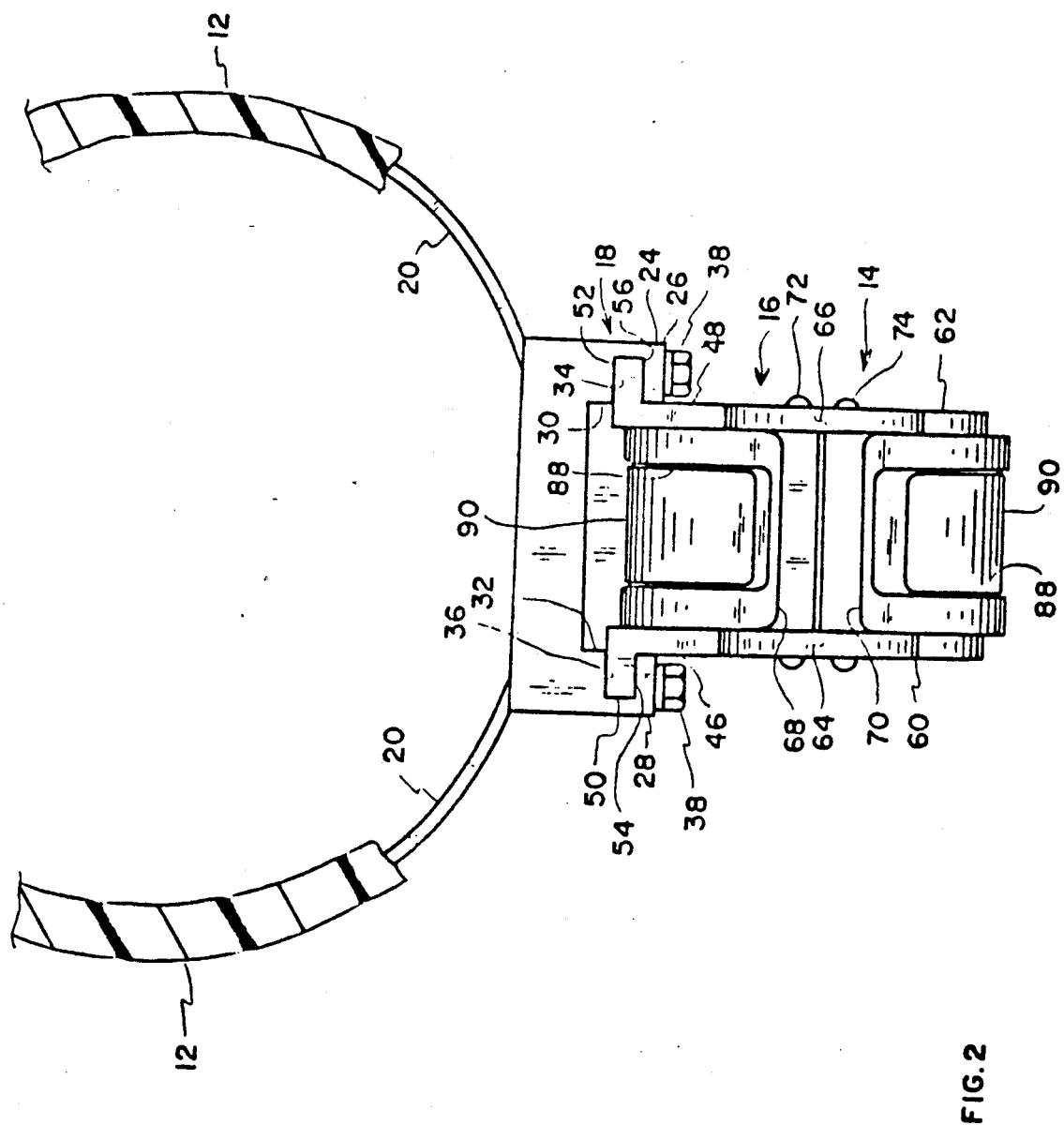
FIG. 2 is a planar view from the effector end of the invention, also partially cut away.
Figure 3:
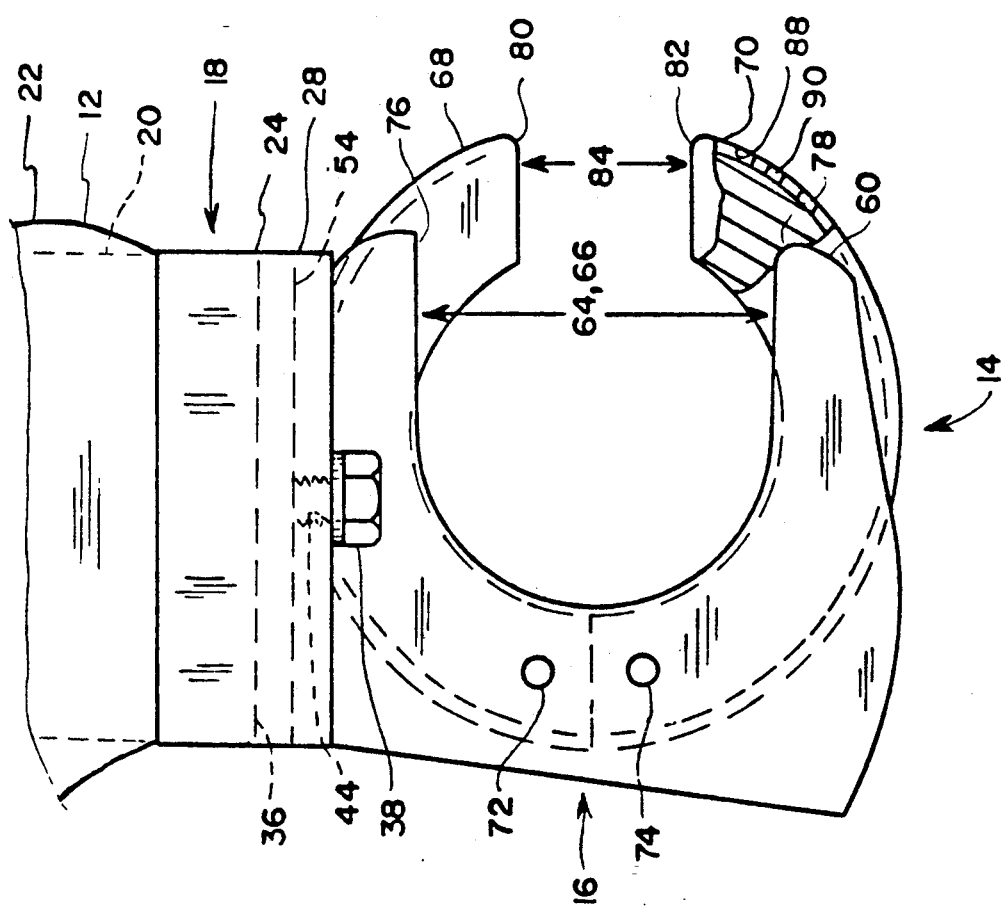
FIG. 3 is a planar view of the effector as seen from one side.

Effector assembly 14, as shown in the drawings, is constructed of two parts, a detachable effector 16 and a mount 18. Mount 18 is provided with anchor bands 20 of a semi-circular or circular shape, with bands 20 embedded in body 12 and wrapped with fiberglass netting 19 utilizing the "hand-lapped" construction described above. Bands 20 are positioned adjacent to each 22 of body 12 and are set in body 12 to partially or wholly encircle sides of body 12 (dotted lines) such that mount 18 is offset from an axis 24 longitudinally extending through body 12. Thus, with plastic-coated fiberglass webbing wrapped around anchor band 20 and set in body 12 as described, a tough, durable anchoring is provided for mount 18. On the other side of mount 18 is a receptacle 24 having opposed, downwardly-extending, elongated receiving lugs 26 and 28 (FIGS. 1 and 2). Lugs 26 and 28 each are constructed with inner facing walls 30 and 32 (FIG. 2), respectively, with opposed grooves 34 and 36 cut in facing walls 30 and 32. Bolts 38 serve to lock effector 16 in place and are threaded into threaded openings 44 (only one shown in FIG. 3) in lower sides of lugs 26 and 28, with openings 44 communicating as shown with grooves 34 and 36.

For removably mounting effector 16 in mount 18 and referring to FIG. 2, a quick disconnect means having opposed upper edges 46 and 48 of effector 16 are each provided with elongated, outwardly-extending opposed rails or flanges 50 and 52 which slidably engage grooves 34 and 36 of lugs 26 and 28. Bolts 38, when tightened, bear on bottoms 54 and 56 of rails or flanges 50 and 52, clamping effector 16 in place in receptacle 24.

Effector 16 is further configured with spaced downwardly-extending supports or support arms 60 and 62, which are formed on and extend from upper edges of band 48, respectively. Supports 60 and 62 are provided with aligned C-shaped slots 64 and 66 positioned in supports 60 and 62 such that the open region of slots 64 and 66 faces forward of body 12. Supports 60 and 62 serve to receive weight or other forces applied to effector 16 when a horizontal, tubular member is held in slots 64 and 66.

For generally providing gripped engagement with a tubular handle or object positioned in slots 64 and 66, a pair of opposed, upper and lower half C-shaped clamping or gripping members 68 and 70 are pivotally mounted as shown between supports 60 and 62. Gripping members 68 and 70 pivot around pins 72 and 74 located as shown near the closed ends of slots 64 and 66, which pins extend through supports 60 and 62 and the respective gripping member. Additionally, gripping members 68 and 70 extend circularly past edges 76 and 78 (FIG. 3) of slots 64 and 66 in supports 60 and 62. Alternatively, one or the other of gripping members 68 and 70 may be fixed in place or be integral with supports 60 and 62, with the other gripping member disposed in pivoting relation between supports 60 and 62. Ends 80 and 82 of gripping members 68 and 70 define a gap 84 through which a tubular object is forced into slots 64 and 66.

For providing gripped engagement with a bar or tube, the outer periphery of gripping members 68 and 70 are provided with a groove or recess 88 (FIGS. 2 and 3) within which a C-shaped spring 90 is fitted. Spring 90 serves to bias gripping members 68 and 70 together in closed relation with respect to gap 84, loosely holding or gripping a bar in slots 64 and 66. If desired, frictional or protective pads (not shown) may be placed along inner surfaces of slots 64 and 66 and gripping members 68 and 70 to effect a frictional engagement of a bar or when it is desired not to mar surfaces of the bar. Additionally, the degree of gripping forces exerted by the gripping members may be adjusted by adding additional springs or changing the spring in gripping members 68 and 70 to a stiffer or less stiff spring.

In use, the wearer of the prosthetic device forces a bar or tubular handle, such as the bar on a chainsaw, into gap 84, forcing gripping members 68 and 70 to pivot slightly against spring 90 and admit the bar into slots 64 and 66 of supports 60 and 62. The bar may then be lifted or pushed by the user, with weight associated with the bar, such as a chainsaw, bearing on or against supports 60 and 62. To release the bar, the user forces the bar outward through gap 84 defined by gripping members 68 and 70.

Having thus described our invention and the manner of its use, it is apparent that incidental modifications may be made thereto which fairly fall within the scope of the following appended claims, wherein we claim:

1. A prosthetic device for a below-the-elbow amputee that will allow the amputee to lift and manipulate horizontally disposed bars and tubes, comprising;
   a generally hollow body having an open end disposed to receive a stump of a forearm of the amputee;
   a mounting assembly anchored in an opposite end of said body and having a receptacle on one side, said receptacle being offset from an axis extending through said body; and
   an effector disposed for removable mounting in said receptacle, said effector comprising;
   a pair of support means each defining a C-shaped slot, with an open region of said slot facing forward of said body in a plane along said axis for receiving lifting or pushing forces applied to said bar,
   gripping means including at least one semicircular gripping member positioned between said pair of support means and partially encircling the open region of said slot at one end, defining a gap therein, and disposed for pivotal movement at an opposite end near a closed end of said slot for holding said bar in said slot, and
   biasing means coupled to said gripping member for biasing said gripping member toward said slot, for holding said bar within said slot, whereby as said bar is forced into said gap, said gripping member being urged away from said slot, allowing passage of said bar into or out of said slot.

2. A prosthetic limb as set forth in claim 1 wherein one end of said mounting assembly is provided with opposed semi-circular bands rigidly set by hand lapped construction in sides proximate said opposite end of said body.

3. A prosthetic limb a set forth in claim 1 wherein said effector comprises a pair of opposed, outwardly-extending rails on said effector, and said mounting assembly is provided with opposed, downwardly-extending lugs having inner facing walls, with an aligned groove in each of said facing walls, for receiving said rails, and locking bolts threadably engaging threaded openings in lower sides of said lugs, said openings in communicating relation with said grooves, clamping against said rails and holding said effector in place.

4. A prosthetic limb as set forth in claim 1 wherein said biasing means comprises a semi-circular left spring disposed in a peripheral groove in said gripping member for biasing said gripping member toward said slot.

5. A prosthetic limb as set forth in claim 1 wherein said gripping means comprises a pair of opposed, semi-circular gripping members pivotally mounted between said support members, each pivotally mounted at one end near said closed end of said slot.

6. A prosthetic limb for a below-the-elbow amputee which will allow the amputee to lift and manipulate horizontally disposed bars and tubes comprising;
   a generally hollow body having one end disposed to fit over the stump of a forearm of the wearer;
   a mount anchored in an opposite end of said body, said mount having a receptacle offset from an axle extending through said body; and
   an effector disposed for removable mounting in said receptacle, said effector comprising:
   support means for applying lifting and pushing forces to a bar, said support means having a C-shaped slot for receiving said bar, with an open region of said slot facing forward of said body,
   at least one semi-circular gripping member having one end disposed for partially encircling an open end of said slot and defining a gap therein and pivotally mounted at an opposite end near a closed end of said slot, for holding a bar in said slot, and
   biasing means connected to said gripping member for biasing said gripping member toward said slot and against said bar.

7. A prosthetic limb as set forth in claim 6 wherein said mount comprises a circular band set in said opposite end of said body.

8. A prosthetic mount as set forth in claim 7 wherein said effector comprises opposed, outwardly-extending rails, and said receptacle is provided with opposed lugs having facing surfaces, with opposed grooves in said facing surfaces for receiving said rails.

9. A prosthetic limb as set forth in claim 8 wherein said gripping member comprises a pair of opposed, semi-circular gripping members pivotally mounted at one end near a closed end of said slot.

10. A prosthetic limb as set forth in claim 9 wherein said biasing means comprises a C-shaped leaf spring fitted around an outer periphery of said gripping members.

11. A prosthetic limb as set forth in claim 10 comprising a locking bolt threadably engaging a threaded opening in at least one of said lugs, said opening communicating with one of said grooves, for bearing against one of said rails and locking said effector in said lugs.

12. A prosthetic device for a below-the-elbow amputee that will allow the amputee to lift and manipulate bar-like members, comprising:

a cuff having a closed end and an open end disposed for receiving the stump of a forearm of the amputee;

a support member carried adjacent to said closed end of said cuff and provided with opposed spaced faces, each having a groove therein;

an effector assembly including gripping means for peripherally engaging said bar-like member for gripped engagement therewith; and quick disconnect means secured to said effector assembly comprising a pair of opposed flanges, each disposed for slidable relation in a said groove, and means for securing each said flange in each said groove.

13. A prosthetic device as set forth in claim 12 wherein said gripping means includes a pair of opposed clamping members and biasing means for biasing said clamping members into and out of said gripped engagement.

14. A prosthetic device as set forth in claim 13 including a pair of spaced support arms for support of said gripping means thereon, each said support arm depending from a said flange of said quick disconnect means.

* * * * *